US 8,286,936 B2

(12) United States Patent
Kitani et al.

(10) Patent No.: US 8,286,936 B2
(45) Date of Patent: Oct. 16, 2012

(54) CLOSABLE MALE LUER CONNECTOR

(75) Inventors: Ichiro Kitani, Fukuroi (JP); Shigeaki Funamura, Fukuroi (JP); Norifumi Fujiwara, Fukuroi (JP); Yosuke Sakai, Fukuroi (JP)

(73) Assignee: Tyco Healthcare Group LP, Mansfield, MA (US)

( * ) Notice: Subject to any disclaimer, the term of this patent is extended or adjusted under 35 U.S.C. 154(b) by 967 days.

(21) Appl. No.: 12/295,739

(22) PCT Filed: Mar. 29, 2007

(86) PCT No.: PCT/EP2007/002830
§ 371 (c)(1),
(2), (4) Date: Dec. 16, 2008

(87) PCT Pub. No.: WO2007/112944
PCT Pub. Date: Oct. 11, 2007

(65) Prior Publication Data
US 2009/0177170 A1    Jul. 9, 2009

(30) Foreign Application Priority Data

Apr. 3, 2006  (JP) .............................. 2006-102094
Dec. 27, 2006  (JP) .............................. 2006-350893

(51) Int. Cl.
*F16L 37/28*  (2006.01)
*A61M 5/32*  (2006.01)

(52) U.S. Cl. ............... 251/149.6; 251/149.5; 251/149.1; 251/149.9; 604/134; 604/119; 604/163; 604/162; 604/167.06

(58) Field of Classification Search ............... 251/149.6, 251/149.4, 149.3, 149.1; 604/134, 118, 119, 604/155, 162, 163, 167.01, 167.04, 167.06
See application file for complete search history.

(56) References Cited

U.S. PATENT DOCUMENTS

| | | | | |
|---|---|---|---|---|
| 4,728,075 | A * | 3/1988 | Paradis | 251/122 |
| 5,228,647 | A * | 7/1993 | Ruibal Santome | 251/149.4 |
| 5,253,842 | A * | 10/1993 | Huebscher et al. | 251/149.6 |
| 5,893,391 | A * | 4/1999 | Jenski, Jr. | 137/614.04 |
| 6,283,443 | B1 * | 9/2001 | Taneya | 251/149.6 |
| 6,745,998 | B2 * | 6/2004 | Doyle | 251/149.6 |
| 7,140,592 | B2 * | 11/2006 | Phillips | 251/149.6 |
| 2004/0124389 | A1 | 7/2004 | Phillips | |

FOREIGN PATENT DOCUMENTS

| | | |
|---|---|---|
| EP | 0 268 480 | 5/1988 |
| WO | 2005/065767 | 7/2005 |
| WO | 2006/062912 | 6/2006 |
| WO | 20061074935 | 7/2006 |
| WO | 2007/008511 | 1/2007 |

OTHER PUBLICATIONS

International Search Report, dated Jul. 23, 2007.

* cited by examiner

*Primary Examiner* — Len Tran
*Assistant Examiner* — James Hogan
(74) *Attorney, Agent, or Firm* — Lisa E. Winsor, Esq.

(57) ABSTRACT

A closable male luer connector is provided in which an inner portion within the spigot of the connector is movable from a sealing position to an open position on connection of the connector to a female luer connector wherein the movement of the inner portion may be caused by, for example, action of the female connector on a projecting arm or a screw thread arrangement.

7 Claims, 10 Drawing Sheets

CLOSABLE MALE LUER CONNECTOR

TECHNICAL FIELD

The invention relates to a male luer connector attachable to a female luer connector having an arrangement for providing a closure when not connected.

BACKGROUND OF THE INVENTION

In the medical field, a connector for connecting several kinds of medical tubes is used to form a liquid transfusion, a blood transfusion, dialysis, or a blood collection circuits. The representative connector used in such a case is a commonly normalize luer connector having a tapered shape.

The luer connector is generally formed by a female luer connector and a male luer connector, in which one of medical tubes is connected to the male luer connector and the other medical tube is connected to the female luer connector. Further, by coupling the male luer connector with the female luer connector, the one of the medical tubes and the other medical tube are communicated with each other. In this time, the inner peripheral wall of a tapered shape formed to the female luer connector and the outer peripheral wall of a tapered shape formed to a male luer part of the male luer connector are liquid tightly contacted. The male luer connector is fixed to the female luer connector with this contact condition, whereby the coupling between the male luer connector and the female luer connector is completed and the liquid tightness for connecting the medical tubes can be secured.

The female luer connector may include a normally closed valve mechanism mounted to the opening portion thereof, in which the valve mechanism is closed when the male luer connector is not coupled to the female luer connector. Therefore, a liquid within the medical tubes is not leaked from the female luer connector when it is not coupled with the male luer connector. On the other hand, when the female luer connector is coupled to the male luer connector, the above valve mechanism is opened to communicate the female luer connector with the male luer connector. In this condition, when the liquid is delivered from one of the medical tube connected to the male luer connector to the male luer connector, the liquid flows from the male luer connector to the female luer connector and further flows from the female luer connector to the other medical tube connected to the female luer connector. In this way, the one of the medical tube connected to the male luer connector is communicated with the other medical tube connected to the female luer connector.

For such a luer connector, for example, JP 07-505064 discloses a luer connector in which an elastic silicone sealer is attached to the opening portion of the female luer connector and a spike part having a sharp tip is placed within the silicone sealer. Within the spike part, a flow path is formed and the spike part has an opening near the tip end. The medical tube is connected to the basal end portion of the spike part. When the male luer part of the male luer connector presses the tip end opening of the female luer connector, the elastic silicone sealer is opened to couple with the male luer part.

SUMMARY OF THE INVENTION

As described in above, while the female luer connector having the normally closed valve mechanism mounted thereon has been known, such a valve mechanism is not mounted on the male luer connector. Accordingly, there is a fear of generation of bacteria at the tip end opening of the male luer connector. Also, there is a fear that the liquid medicine is spilled out of the tip end opening of the male luer connector at priming process and bacteria may be brood at that portion.

The invention has been made in the light of these problems and the object of the invention is to provide a male luer connector in which the opening can be maintained bacteria free.

In order to achieve the above object, the configurational characteristics of the male luer connector in accordance with the invention is that the male luer connector is connected to a first tube member and coupled to the female luer connector to communicate a flow path space within the first tube member with a flow path space within a second tube member connected to the female luer connector, said male luer connector comprising a male luer part including a tapered outer peripheral wall formed so as to be tapered as toward the tip end side and liquid tightly contacted with the tapered inner peripheral wall formed to the female luer connector, a side wall having an inner wall forming an inner space, an outlet opening formed at the smaller diameter surface of the side wall for communicating the inner space with the exterior; and a body tube of a tube member provided with a flow path for communicating therein, said body tube having openings for communicate the flow path for communication with the exterior at one end and the other end thereof, said one end being movably inserted into the inner space and the other end being connectable to said first tube member, said body tube further comprising a male luer part sealing means for liquid tightly sealing the outlet opening by moving within the inner space.

In the male luer connector of the present invention having the above characteristic, one end of the body tube inserted into the inner space in the male luer part is moved in the predetermined direction, whereby the male luer part sealing means formed at the one end liquid tightly seal the outlet opening formed at the smaller diameter surface of the male luer part. In this way, since the outlet opening of the male luer part to be the outlet of the liquid is liquid tightly sealed, the outlet opening can be maintained bacteria free while being unused. Further, in the state where the outlet opening is liquid tightly sealed by the male luer sealing means, when one end of the body tube is moved in the opposite direction of the predetermined direction in the inner space of the male luer part, the outlet opening is opened by deviating the male luer sealing means therefrom. Therefore, when the male luer connector is coupled to the male luer connector, the liquid can be flowed to the female luer connector by opening the outlet opening in the course in above.

According to the invention, the outlet opening is liquid tightly sealed and opened by moving one end of the body tube in the inner space of the male luer part, therefore, the body tube can not be exposed to the outer of the male luer part, in particular, to the area beyond the smaller diameter surface of the male luer part. Herein, in the state where the male luer connector and the female luer connector are coupled to each other, the area beyond the smaller diameter surface of the male luer part is to be a space within the female luer connector, thus, when the components of the male luer connector are exposed to the space in the female luer connector for opening the outlet opening, the exposed components can interfere the components of the female luer connector to cause motion failure thereof. For this point, by the present invention having the above configuration, the outlet opening can smoothly be opened without interference with the female luer connection. The explanation "liquid tightly seal the opening" herein means "the opening is occluded so as to block the communication of the liquid via the opening". Therefore, the invention may be configured such that when the outlet opening is liquid tightly sealed by the male luer part sealing means, the liquid within the inner space can be prevented from discharging out through the outlet opening and the gas within the inner space can be emitted from the outlet opening.

In this case, when the male luer part sealing means liquid tightly seals the outlet opening, the opening formed at one end of the body tube is preferably opened into the inner space of the male luer part. By this configuration, even though the liquid flowing the communicating flow path in the body tube is ran out of the opening formed at the one end of the body tube, the ran out liquid only enters the inner space of the male luer part, thereby preventing the liquid from leaking out of the male luer part through the outlet opening. Further, the male luer part may include a body tube sealing means for liquid tightly sealing the opening formed at the one end of the body tube as the male luer part sealing means liquid tightly seals the outlet opening. Upon the opening formed at the one end of the body tube is liquid tightly sealed by the body tube sealing means at the same time of liquid tightly sealing the outlet opening by the male luer part sealing means, the leakage of the liquid from the body tube can surely be prevented. Moreover, by liquid tightly sealing opening by each other, the contamination by another liquid medicine from the outside into the inner space of the male luer part can certainly be prevented.

While many shapes for the body tube sealing means can be considered, it is preferred to provide a column formed by radially crossing the male luer part at the outlet opening, then, to form the body tube sealing means to that column. Since it may be relatively easy to form such a column to the opening, the manufacturing cost of the body tube sealing means can be reduced. Further, the cross section is formed so as to be contained in the column in above so that the opening formed at one end of the body tube can be liquid tightly sealed by the column. Also, when the column is formed in such a way, since the outlet opening is divided into two parts by the column, it is preferred to provide a projection piece having the same cross section as that of the divided cross section at the one end of the body tube.

To at least one of the male luer part sealing means and the body tube sealing means, a gas permeable air filter to which the gas can be passed but the liquid impossible to be passed may be attached. When the gas permeable air filter is attached to the male luer part sealing means, the gas within the male luer part can be discharged to the outside through the gas permeable air filter, while the liquid is not discharged to the outside. Therefore, by priming with the outlet opening of the male luer part liquid tightly sealed by the male luer sealing means, only the gas such as air resided within the male luer part, the body tube, or the tube member to be connected to the body tube can be discharged from the outlet opening to the outside. Herein, the explanation "the liquid impossible to be passed through" includes not only the case where the liquid can not be passed through at all but also the case where the liquid substantially impossible to be passed through (small amount of the liquid may be passed though but apparently impossible to be passed due to the very slow passing rate).

Also, the male luer connector of the present invention may be provided with a seal member such as O ring between the inner wall and the periphery of the body tube. By providing the seal member at that poison, the leakage of the liquid out of the male luer part can be prevented by the present of the seal member even though the liquid flows from the opening formed at one end of the body tube to the inner space of the male luer part while the outlet opening is liquid tightly sealed with the male luer sealing member. Further, the male luer connector of the invention may include an activating means for activating the body tube to move in the axis direction such that the male luer part sealing means liquid tightly seals the outlet opening. By having such an activating means, it can be maintained that the male luer sealing means always liquid tightly seals the outlet opening.

Moreover, the male luer connector of the present invention may include a cooperative mechanism for moving the body tube such that the outlet opening is released from the condition where it is liquid tightly sealed by the male luer sealing means as cooperated with the movement of the male luer connector at the coupling with the female luer connector. In order to couple the female luer connector to the male luer connector, while different operations are required: to contact the female luer connector with the male luer connector by approaching each other and to open the outlet opening by releasing the liquid tight sealing of the outlet opening by the male luer part sealing means, by using the movement force of the female luer connector by the cooperative mechanism to move the body tube and to release the liquid tight sealing of the outlet opening with the use of the male luer part sealing means, thereby easily coupling to the female luer connector without such different operations as in above.

In this case, the cooperative mechanism may be fixed to the body tube as well as comprising a support arm placed so as to contact with the end surface of the female luer connector at the coupling of the female luer connector. By this configuration, when the female luer connector is approached to the male luer connector, the support arm is contacted to the end surface of the female luer connector to receive the moving force of the female luer connector. Also, when the female luer connector is moved with the contact as maintained, the moving force is transmitted to the body tube fixing the support arm to move the body tube.

The male luer connector in accordance with the invention may further comprise a lock member having a first inner threaded part capable of being helically connected to the female luer connector, when said first threaded part being helically engaged with the female luer connector, the male luer part is fixed to the female luer connector while tapered outer peripheral wall is contacted to the inner periphery wall of the female luer connector. By this lock member, the connection of the male luer connector with the female luer connector can be secured to prevent the connection between the male luer connector and the female connector from easily being released by an unexpected external force.

In this case, the lock member is capable of being helically fitted to the outer periphery of the body tube, as well as, the lock member may include a second inner threaded part in which a lead in the same direction of the lead of the first inner threaded part. That is, when the first inner thread portion is a right hand screw, then, the second inner threaded part is also a right hand screw, conversely, when the first inner thread portion is a left hand screw, then, the second inner threaded part is also a left hand screw. By such a configuration, at the same time of that the first inner threaded part is helically connected with the female luer connector as the female luer connector is approaching the male luer connector, the body tube is moved to deviated from the male luer connector. Therefore, the operation for fixing the female luer connector to the male luer connector and the operation for separating the male luer part sealing means from the outlet opening to open the outlet opening by the movement of the body tube can be performed at the same time by the rotational motion of the lock member.

Further, another characteristic of the male luer connector in accordance with the invention is that the male luer connector is connected to a first tube member and coupled to the female luer connector to communicate a flow path space within the first tube member with a flow path space within a second tube member connected to the female luer connector, said male luer connector comprising a body tube of a tube member provided with a flow path for communicating therein, said body tube having openings for communicate the flow path for communication with the exterior at one end and the other end thereof, said one end being movably inserted into the inner space and the other end being connectable to said first tube member, said body tube further comprising a male luer part sealing means for liquid tightly sealing the outlet opening by moving within the inner space; and a male luer part including a tapered outer peripheral wall formed so as to be tapered as toward the tip end side and liquid tightly contacted with the tapered inner peripheral wall formed to the female luer connector, a side wall having an inner wall forming an inner space, an outlet opening formed at the smaller diameter surface of the side wall for communicating the inner space with the exterior, and a body tube sealing means formed at the outlet opening or the inner wall for liquid tightly sealing the opening formed at one end of the body tube as the body tube is moved within the inner space.

In the male luer connector of the present invention having the above characteristic, one end of the body tube inserted into the inner space in the male luer part is moved in the predetermined direction, whereby the male luer part sealing means formed at the one end liquid tightly seal the outlet opening formed at the smaller diameter surface of the male luer part. In this way, since the outlet opening of the male luer part to be the outlet of the liquid is liquid tightly sealed, the outlet opening can be maintained bacteria free while being unused.

Further, another characteristic of the male luer connector in accordance with the invention is that the male luer connector is connected to a first tube member and coupled to the female luer connector to communicate a flow path space within the first tube member with a flow path space within a second tube member connected to the female luer connector, said male luer connector comprising a male luer part including a tapered outer peripheral wall formed so as to be tapered as toward the tip end side and liquid tightly contacted with the tapered inner peripheral wall formed to the female luer connector, a side wall having an inner wall forming an inner space, an outlet opening formed at the smaller diameter surface of the side wall for communicating the inner space with the exterior; a connector body in which one end is connected to the male luer part to form therein a space portion for communicate with the inner space of said male luer part and the other end is capable of being connected to the first tube member; and a moving body tube of a tube member provided with a flow path for communicating therein, said body tube having openings for communicate the flow path for communication with the exterior at one end and the other end thereof, said one end being movably inserted into the inner space and the other end being connectable to said first tube member, said body tube further comprising a male luer part sealing means for liquid tightly sealing the outlet opening by moving within the inner space.

In the male luer connector of the present invention having the above characteristic, one end of the body tube inserted into the inner space in the male luer part is moved in the predetermined direction, whereby the male luer part sealing means formed at the one end liquid tightly seal the outlet opening formed at the smaller diameter surface of the male luer part. In this way, since the outlet opening of the male luer part to be the outlet of the liquid is liquid tightly sealed, the outlet opening can be maintained bacteria free while being unused. Further, in the state where the outlet opening is liquid tightly sealed by the male luer sealing means, when one end of the body tube is moved in the opposite direction of the predetermined direction in the inner space of the male luer part, the outlet opening is opened by deviating the male luer sealing means therefrom. Therefore, when the male luer connector is coupled to the male luer connector, the liquid can be flowed to the female luer connector by opening the outlet opening in the course in above.

According to the invention, the outlet opening is liquid tightly sealed and opened by moving one end of the body tube in the inner space of the male luer part, therefore, the body tube can not be exposed to the outer of the male luer part, in particular, to the area beyond the smaller diameter surface of the male luer part. Herein, in the state where the male luer connector and the female luer connector are coupled to each other, the area beyond the smaller diameter surface of the male luer part is to be a space within the female luer connector, thus, when the components of the male luer connector are exposed to the space in the female luer connector for opening the outlet opening, the exposed components can interfere the components of the female luer connector to cause motion failure thereof. For this point, by the present invention having the above configuration, the outlet opening can smoothly be opened without interference with the female luer connection.

In this case, the male luer connector is preferred to further comprise an elastic seal member including a stretch hole provided at the portion corresponding to the other end of the moving body tube in the connector body so as to activate the moving body tube to one direction to occlude the communicating flow path and to the other direction to open the stretch hole; and a cooperative mechanism for moving the body tube such that the outlet opening is released from the condition where it is liquid tightly sealed by the male luer sealing means as cooperated with the movement of the male luer connector at the coupling with the female luer connector.

In this male luer connector, the male luer part is provided so as to protrude from one end of the connector body connected to the first tube member at the other end thereof. Further, within the male luer part, the moving body tube is provided to slidably move in the axis direction. Also, at the portion corresponding to the other end of the moving body tube within the connector body, the elastic seal member having the stretch hole is provided so as to activate the moving body tube in one direction and to close the communicating flow path in the moving body tube. When the moving body tube is activated to one direction by the elastic seal member, the outlet opening of the male luer part is liquid tightly sealed by the male luer part sealing means. Further, the male luer connector includes the cooperative mechanism for moving the moving body tube to release the liquid tight sealing of the outlet opening by the male luer part sealing means.

Therefore, when the male luer connector is not connected to the female luer connector, the elastic seal member is not receive any external force which remains the stretch hole of the elastic seal member closed, thereby occluding the communicating flow path within the moving body tube with the elastic seal member. Accordingly, when the priming is performed, there is no fear that the liquid medicine is spilled out of the tip end opening of the male luer connector. As a result, it can be prevented that the liquid medicine is spilled out to adhere the outer surface of the male luer connector, or bacteria is brood at the adhered portion. Further, the spilled the liquid medicine can be reduced to save the liquid medicine.

The outer peripheral surface of the male luer part is formed in a curved surface having a taper being tapered as closed to the tip end, and the inner peripheral surface of the female luer connector is formed in a curved surface so as to liquid tightly contact with the outer peripheral surface of the male luer part. When the inner peripheral surface of the female luer connector is liquid tightly contacted with the outer peripheral surface of the male luer part by inserting the tip end of the male luer part into the female luer connector to engage the female luer connector with the male luer part, the moving body tube is moved the other direction by the action of the cooperative mechanism and the elastic seal member is pushed by the moving body tube to open the stretch hole.

In the other word, when the inner peripheral surface of the female luer connector is liquid tightly contacted with the tip end of the outer peripheral surface of the male luer part, the moving body tube is pushed by the female luer connector to open the outlet opening of the male luer part and the stretch hole of the elastic seal member. Accordingly, since the first tube member and the second tube member are communicated with each other through the male luer connector and the female luer connector, a liquid such as a liquid medicine can be flowed therethrough. Also, then, the opening of the stretch hole of the elastic seal member is required to have a size to properly pass the liquid.

Further, in this case, since the moving body tube is moved by the use of the moving force of the female luer connector with the cooperative mechanism, whereby the male luer part sealing means releases the liquid tight seal of the outlet opening, as well as opens the stretch hole of the elastic seal means, the requirement of different operations: to connect the male luer connector with the female luer connector; and to open the outlet opening of the male luer part and the stretch hole of the elastic seal member, thereby easily coupling to the female luer connector.

In this case, the cooperative mechanism is fixed to the moving body tube as well as comprising a support arm placed so as to contact with the end surface of the female luer connector at the coupling of the female luer connector. By this configuration, when the female luer connector is approached to the male luer connector, the support arm is contacted to the end surface of the female luer connector to receive the moving force of the female luer connector. Also, when the female luer connector is moved with the contact as maintained, the moving force is transmitted to the body tube fixing the support arm to move the body tube.

In the female luer connector in accordance with the invention, the male luer part may include a body tube sealing means for liquid tightly sealing the opening formed at the one end of the body tube as the male luer part sealing means liquid tightly seals the outlet opening. Upon the opening formed at the one end of the body tube is liquid tightly sealed by the body tube sealing means at the same time of liquid tightly sealing the outlet opening by the male luer part sealing means, the leakage of the liquid from the body tube can surely be prevented. Moreover, by liquid tightly sealing opening by each other, the contamination by another liquid medicine from the outside into the inner space of the male luer part can certainly be prevented.

To at least one of the male luer part sealing means and the body tube sealing means, a gas permeable air filter to which the gas can be passed but the liquid impossible to be passed may be attached. When the gas permeable air filter is attached to the male luer part sealing means, the gas within the male luer part can be discharged to the outside through the gas permeable air filter, while the liquid is not discharged to the outside. Therefore, by priming with the outlet opening of the male luer part liquid tightly sealed by the male luer sealing means, only the gas such as air resided within the male luer part, the body tube, or the tube member to be connected to the body tube can be discharged from the outlet opening to the outside.

Also, the male luer connector of the present invention may be provided with a seal member such as O ring between the inner wall and the periphery of the body tube. By providing the seal member at that poison, the leakage of the liquid out of the male luer part can be prevented by the present of the seal member even though the liquid flows from the opening formed at one end of the body tube to the inner space of the male luer part while the outlet opening is liquid tightly sealed with the male luer sealing member.

The male luer connector in accordance with the invention may further comprise a lock member having a first inner threaded part capable of being helically connected to the female luer connector, said first threaded part being helically engaged with the female luer connector, whereby the male luer part is fixed to the female luer connector while tapered outer peripheral wall is contacted to the inner periphery wall of the female luer connector. By this lock member, the connection of the male luer connector with the female luer connector can be secured to prevent the connection between the male luer connector and the female connector from easily being released by an unexpected external force.

BRIEF DESCRIPTION OF THE DRAWINGS

The invention will now be described, by way of example only, with reference to the accompanying drawings in which.

PREFERRED EMBODIMENTS OF THE INVENTION

First Embodiment

Figure 1:
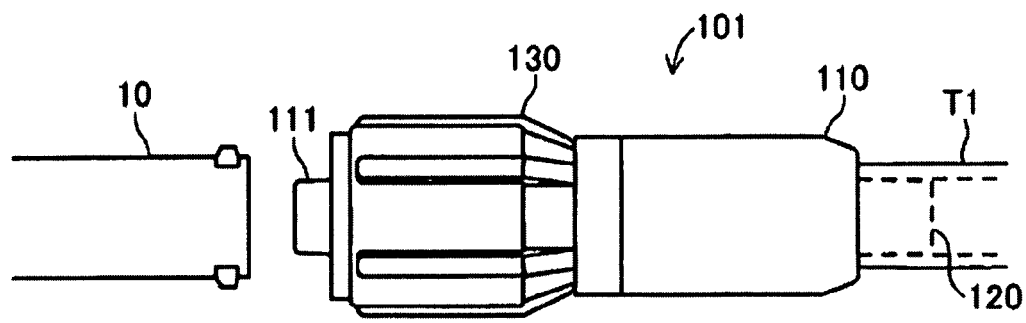
FIG. 1 is a plane view illustrating the male luer connector of a first embodiment in accordance with the present invention.
Figure 2:
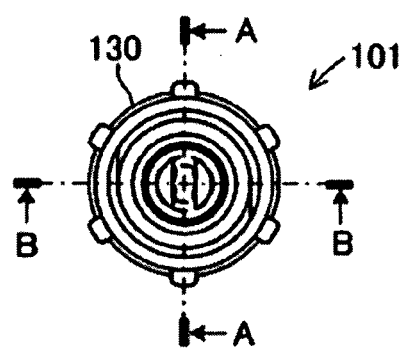
FIG. 2 is a front view illustrating the male luer connector of the first embodiment in accordance with the present invention.
Figure 3:
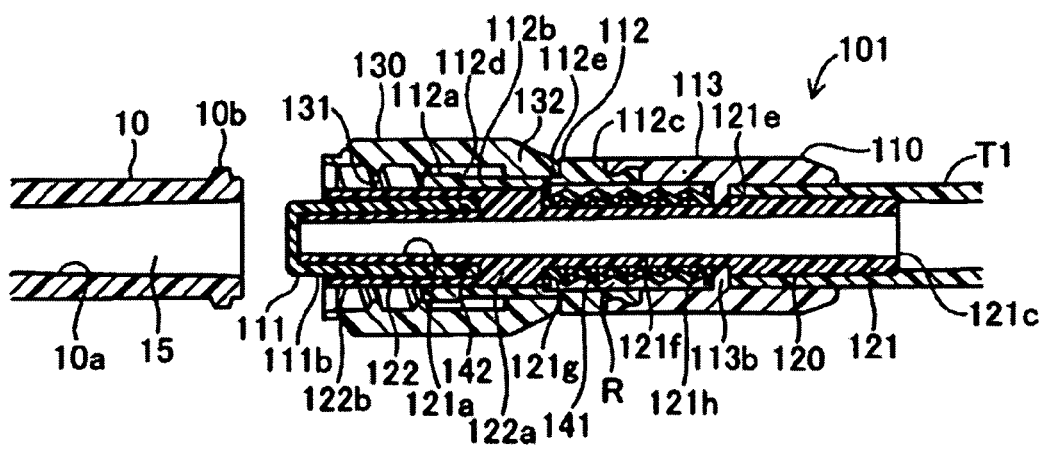
FIG. 3 is a cross sectional view illustrating a cross section at A-A in FIG. 2.
Figure 4:
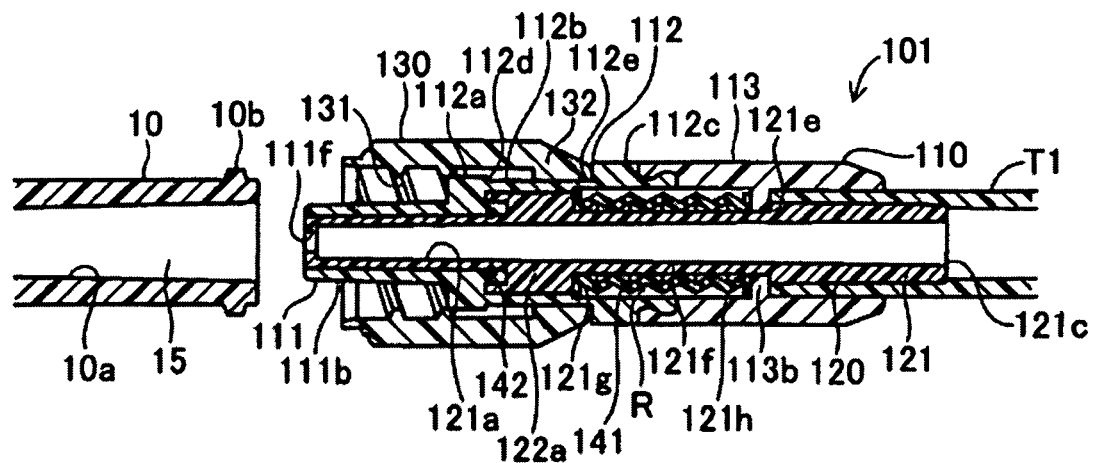
FIG. 4 is a cross sectional view illustrating a cross section at B-B in FIG. 2.

The male luer connector in accordance with the invention will now be explained in detail with reference to the accompanied drawing in below. FIG. 1 is a plane view of the luer connector of the first embodiment in accordance with the invention; FIG. 2 is a front view, FIG. 3 is a cross sectional view sectioned at A-A in FIG. 2; FIG. 4 is a cross sectional view sectioned at B-B in FIG. 2. As shown in FIG. 1, a male luer connector 101 of the embodiment is connected to a first tube member T1 and coupled to a female luer connector 10 to communicate a flow path space within the first tube member and a flow path within a second tube member (not shown) connected to the female luer connector 10. The male luer connector 101 comprises an outer cylinder part 110, an inner cylinder part 120 and a lock ring 130.

Figure 5:
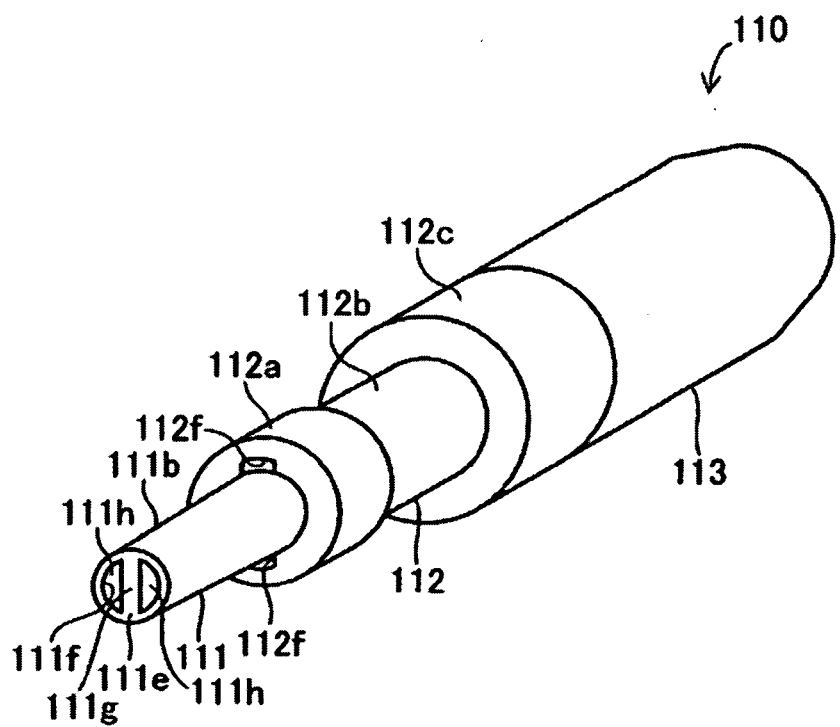
FIG. 5 is a perspective view illustrating the outer cylinder of the first embodiment in accordance with the present invention.
Figure 6:
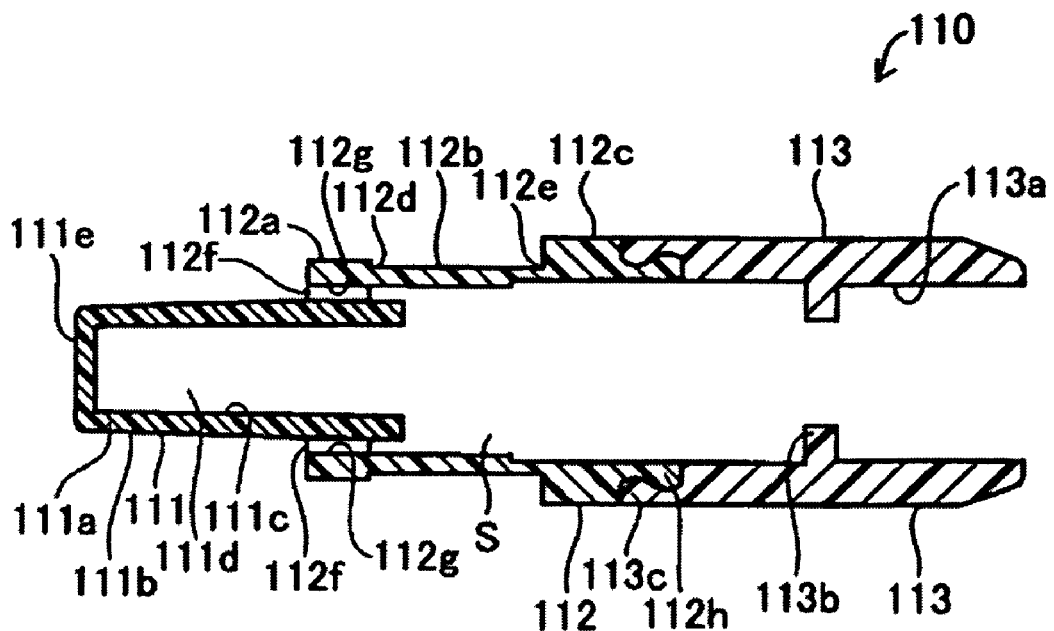
FIG. 6 is a cross sectional view illustrating the outer cylinder of the first embodiment in accordance with the present invention.

FIG. 5 is a generally perspective view of the outer cylinder part 110 and FIG. 6 shows only the outer cylinder part 110 of the components illustrated in the cross sectional view of FIG. 3. As shown in FIGS. 3 to 6, the outer cylinder 110 includes a male luer part 111, a ring holding part 112 and a holding part 113 and is formed into a cylindrical shape with steps as over viewed. The male luer part 111 is placed at the tip end (in the left end in FIGS. 3, 4, and 6) of the outer cylinder 110 to be contacted with the inner wall of the female luer connector 10. The ring holding part 112 is connected to the male luer part 111 to hold a lock ring as described in below. The holder part 113 is formed at the basal end of the outer cylinder 110 which is to be a portion for holding the male luer connector 101 by a user.

As shown in FIG. 6, the male luer part 111 is formed into a cylindrical form having a side wall 111a. The side wall 111a comprises a tapered outer peripheral wall 111b formed so as to tapered as reached to the tip end (the left side in the figure) and an inner side wall 111c that is opposed surface to the tapered outer peripheral wall 111g for forming an inner space in the inner periphery. The tapered outer peripheral wall 111b is a surface that can be contacted with the tapered inner peripheral wall 10a formed to the female luer connector 10. Since the tapered outer peripheral wall 111b is tapered as described in above, the tip end surface of the side wall 111a provides a smaller diameter surface 111e in which the outer diameter is the smallest. Also, the basal end of the side wall 111a (the right side in the figure) is opened from which a body tube 121 described in below is inserted into the inner space 111d.

Figure 7:
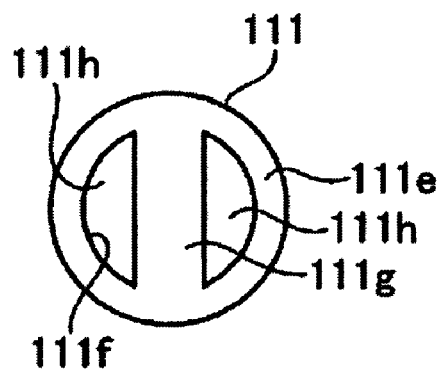
FIG. 7 is a front view illustrating the male luer part of the first embodiment in accordance with the present invention.

FIG. 7 is an enlarged view of the smaller diameter surface 111e in the front view. As shown in FIG. 7, to the smaller diameter surface 111e, an outlet opening 111f is formed, provided with a column 111g so as to be radially transverse the outlet opening 111f. Accordingly, the outlet opening 111f is divided into two portions by the column 111g so that two half circle like gaps 111h are opposed to each other by the edge of the opening of the outlet opening 111f. As apparent from the figure, the column 111g is vertically formed to connect the upper and the lower of the smaller diameter surface 111e in the figure. Also, the column 111g is formed not all over the inner space 111d but adjacent to the outlet opening 111f.

As shown in FIG. 6, the ring holding part 112 comprises a first cylinder 112a, second cylinder 112b and a third cylinder 112c. The first cylinder 1112a is radially outwardly extended from the tapered outer peripheral wall of the male luer part 111 and formed into a coaxial cylinder of the male luer part 111. The second cylinder 112b and the third cylinder 112c are cylinder and connected coaxially to the first cylinder 112a in series. As shown in FIGS. 5 and 6, outer diameters of the first cylinder 112a and the third cylinder 112c are greater than that of the second cylinder, whereby a first step 112d is formed in the circumference direction at the boundary between the first cylinder 112a and the second cylinder 112b and a second step 112e is formed in the circumference direction at the boundary between the second cylinder 112b and the third cylinder 112c.

Further, as shown in FIGS. 5 and 6, one end surface of the first cylinder 112a (end surface faced to the male luer part 111) is provided with two windows 112f opened to the exterior. These windows 112f are formed so as to have the predetermined length along the outer periphery of the male luer part 111 and the predetermined width in the radial direction. Also, these two windows 112f are formed with the space of the angle of the 180 degrees so as to be symmetry relative to the axis of the first cylinder 112a. A pathway 112g is formed so as to extend from these windows 112f to the first cylinder 112a. The pathway 112g, as shown in FIG. 6, communicates with the space in the inner periphery of the second cylinder 112b.

The holder 113 is connected to the third cylinder 112c and formed so as to have the outer diameter equal to that of the third cylinder 112c. Also, the holder 113 include an inner wall 113a forming a cylindrical space and an annular projection 113b projecting from the inner wall 113a in the radial direction therein. Further, as shown in FIG. 6, at the connecting end of the holder 113 to the third cylinder 112c, a connector 113c having a constriction in which the inner diameter is smoothly increased or decreased along the axial direction is formed. On the other hand, at the connecting end of the third cylinder 112c to the holder 113, a connector 112h having a constriction and a complemented form to the connector 113c is formed. Further, by engaging these connectors 113c and 112h with each other, the holder 113 is secured to the third cylinder 112c.

Both the ring holding part 112 and the holder 113 are formed into a cylinder in which a space S is formed. The space S, as shown in FIG. 6, communicates with the inner space 111*d* of the male luer part 111. Also, the pathway 112*g* formed in the first cylinder 112*a* is opened to this space S.

Figure 8:
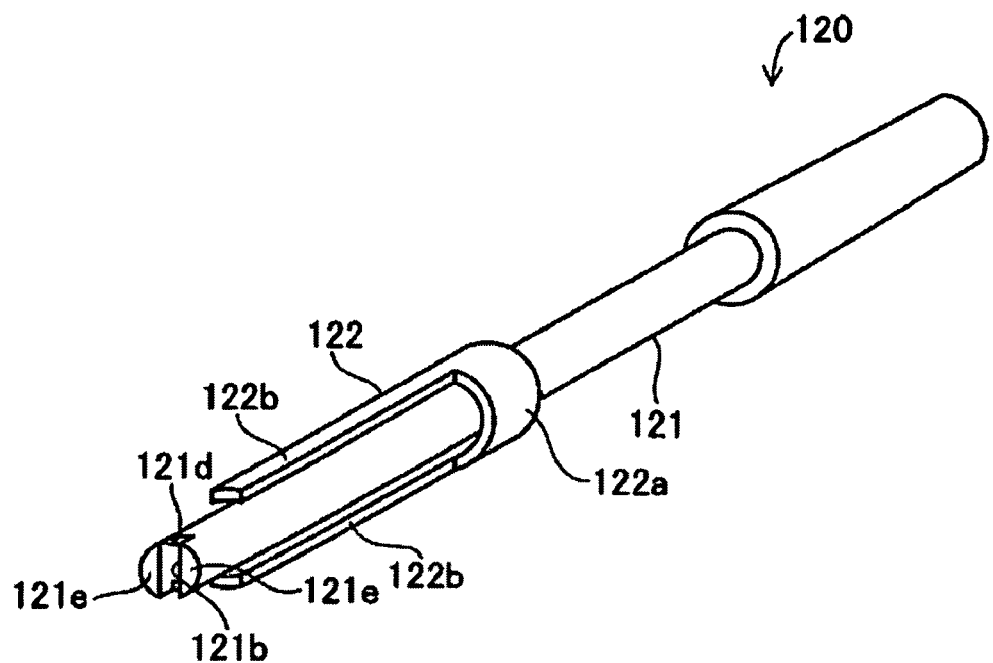
FIG. 8 is a perspective view illustrating the inner cylinder of the first embodiment in accordance with the present invention.
Figure 9:
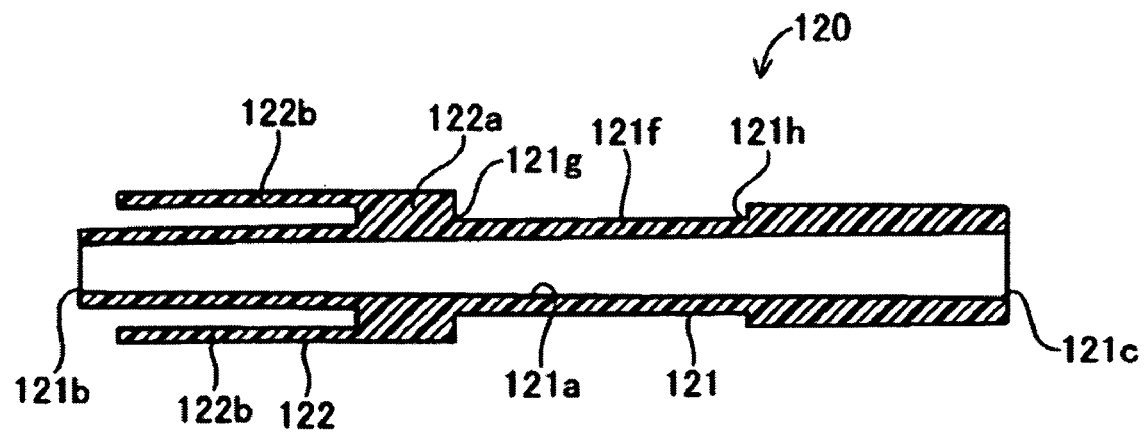
FIG. 9 is a cross sectional view illustrating the inner cylinder of the first embodiment in accordance with the present invention.

FIG. 8 is a generally perspective view of the inner cylinder 120, FIG. 9 shows only the inner cylinder 120 of the components illustrated in the cross sectional view of FIG. 3. As shown in FIGS. 3, 4, 8 and 9, the inner cylinder 120 comprises the body tube 121 formed into a narrow stepped cylinder and a support arm 122 formed on the outer periphery of the body tube 121. Within the body tube 121, a flow path 121*a* is formed. The flow path 121*a* corresponds to the communicating flow path of the present invention and is formed along the axial direction of the body tube 121. The body tube 121 includes a first opening 121*b* and a second opening 121*c*. The first opening 121*c* is formed at one end of the body tube 121 (the left side end in FIGS. 4 and 9). The second opening 121*c* is formed at the other end of the body tube 121 (the right side end in FIGS. 3, 4, and 9). The first tube member T1 is connected to the other end, whereby the flow path space within the first tube member T1 is communicated with the space within the flow path 121*a* of the body tube 121 through the second opening 121*c*.

Figure 10:
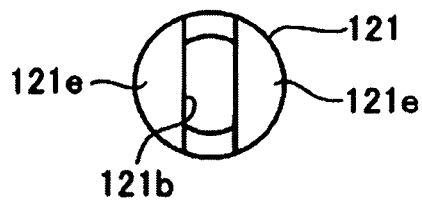
FIG. 10 is a front view illustrating the body tube of the first embodiment in accordance with the present invention.

FIG. 10 is an enlarged view where the first opening 121*b* is viewed from the front. As shown in FIG. 10, the first opening 121*b* is formed to have vertical both edges and concaved or arc shaped upper and lower edges. Therefore, the cross sectional figure surrounded by the first opening 121*b* is a drum like form with the upper and the lower barreled. The cross sectional figure of the space within the flow path 121*a* formed within the body tube 121 is similar to the drum like form in above. Further, as shown in FIG. 8, a notch 121*d* is formed along the axial direction from the first opening 121*b* to the body tube 121 and, at one end of the body tube 121, two half cylindrical projections 121*e* are formed by the notch 121*d*. The cross sectional forms of these projections 121*e* are similar to two half circular gaps 111*h* surrounded by the opening edge of the outlet opening 111*f* formed by the smaller diameter surface 111*e* of the male luer part 111.

The support arm 122 includes a support 122*a* formed to be fixed to the outer periphery of the body tube 121 and radially outwardly extended therefrom and two arms 122*b* extended from the support 122*a* to the second opening 121*b* along the axial direction of the body tube 121. These two arms 122*b* are attached to the support 122*a* so as to be symmetrical relative to the body tube 121 with a space of the angle of 180 degrees, in which the tip end thereof is extended to near the first opening 121*b* not over the first opening 121*b* of the body tube 121. The support arm corresponds to the cooperative mechanism of the present invention. The support arm 122 may be formed integrally with or separately from the body tube 121.

Figure 11:
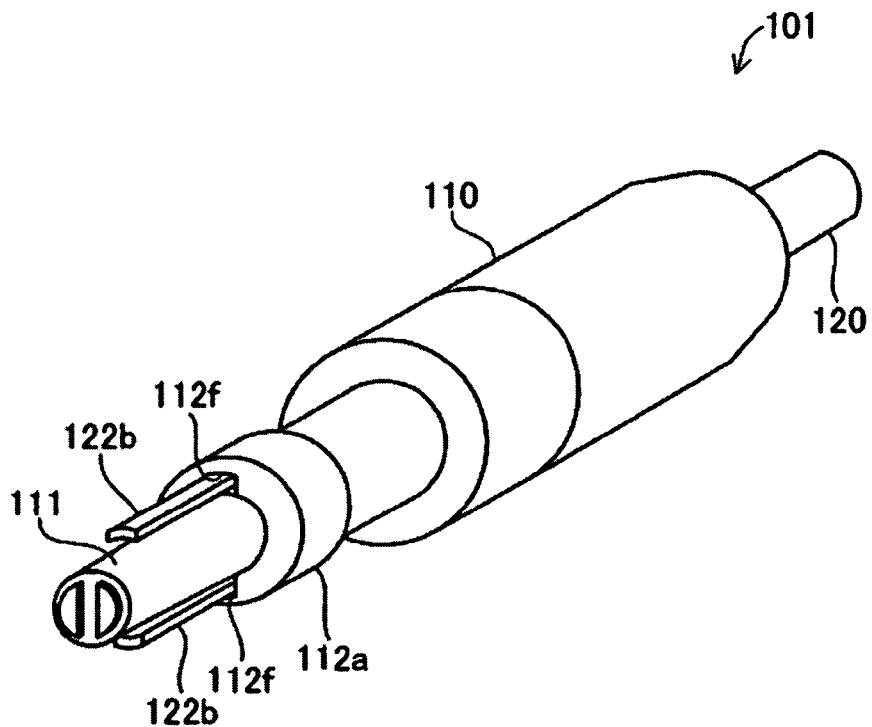
FIG. 11 is a perspective view illustrating the outer cylinder being inserted into the inner cylinder.

As shown in FIGS. 3 and 4, the inner cylinder 120 is inserted into the outer cylinder 110 axially movable. In this time, the portion from the first opening 121*b* (not shown in FIGS. 3 and 4) to the position where the support 122*a* of the support arm 122 is contained within the opening of the basal end of the male luer part 111 through the inner space 111*d* (shown in FIG. 6) and the other portion illustrated in the right side in the figures is contained in the ring holding part 112 and the space S formed on the inner periphery of the holder 113 (see FIG. 9). Further, the support arm 122 is protruded to the exterior of the outer cylinder 110 through the pathway 112*g* formed within the first cylinder 112*a* (see FIG. 6) from the space S. FIG. 11 is a perspective view illustrating the condition where the inner cylinder 120 is inserted. As shown in FIG. 11, the arms 122*b* of the support arm 122 are provided so as to project to the windows 112*f* formed at the end surface of the first cylinder 112*a* and axially projected to the outer cylinder 110. Also, as shown in FIGS. 3 and 4, between the portion near the basal end of the inner wall 111*c* of the male luer part 111 and the outer periphery portion into which the body tube 121 is inserted into the male luer part 111, the O ring 142 is fitted. By this O ring 142, the liquid leakage between the outer wall surface of the body tube 121 and the inner wall 111*c* of the male luer part 111.

As show in FIGS. 3, 4 and 9, near the axial center of the body tube 121, a smaller diameter part 121*f* where the outer diameter is reduced is formed. At both end relative to the axis of the smaller diameter part 121*f*, a third step 121*g* and a forth step 121*h* are formed in the circumference direction. Also, a ring shaped space R is formed between the smaller diameter 121*f* and the inner wall of the outer cylinder 110 while the inner cylinder 120 is inserted into the outer cylinder 110, said ring shaped space R being provided with a bellows 141. The bellows 141 is provided to cover the outer periphery of the body tube 121 such that the body tube 121 can be expandable in the axial direction and the one end of the bellows 141 is contacted to the third step 121*g* and the other end is contacted with the annular projection 113*b* of the holder 113 faced to the outer periphery of the smaller diameter part 121*f*. The bellows 141 generates extension force in the condition as illustrated in the figure, thereby pressing the annular projection 113*b* against the forth step 121*h* and activating the body tube 121 to move toward the left in the figure. Accordingly, the first opening 121*b* of the body tube 121 will be moved near the outlet opening 111*f* of the male luer part 111.

Figure 12:
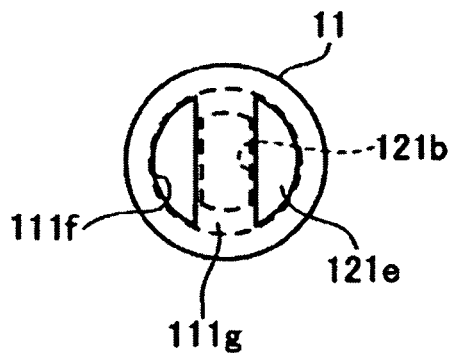
FIG. 12 is a front view illustrating the outer cylinder being inserted into the inner cylinder.

In this time, by the activating force of the bellows 141, two protruding pieces 121*e* (see FIG. 8) formed at one end surface of the body tube 121 are inserted into two half circular gaps 111*h* formed by the opening edge of the outlet opening 111*f* of the male luer part 111 (see FIG. 5), thereby, just occluding two half circular gaps 111*h* with the protruding pieces 121*e* as shown in FIG. 11. As well as, the column 11*g* formed to the outlet opening 111*f* of the male luer part 111 (see FIG. 5) is just fitted within the notch 121*d* formed at the one end surface of the body tube 121 (see FIG. 8), thereby liquid tightly sealing the first opening 121*b* by the column 111*g*. Further, the column 111*g* is contacted with the arc like upper and lower end surfaces forming the flow path 121*a* in the body tube 121 by the notch 121*b*, thereby preventing the body tube 121 from moving further to go out of the outer cylinder 110. In this way, the body tube 121 is moved within the outer cylinder 110 by the activating force of the bellows 141, the protruding pieces 121*e* of the body tube 121 liquid tightly seal the outlet opening 111*f* of the male luer part 111 at the normal time and the column 111*g* of the male luer part 111 liquid tightly seals the first opening 121*b* of the body tube 121. The male luer part 11 in this condition is illustrated in FIG. 12 of the front view. As shown in FIG. 12, the first opening 121*b* is liquid tightly sealed so as to be received in the column 111*g* and the protruding pieces 121*e* are inserted into the outlet opening 111*f* to be liquid tightly sealed. At that time, the outer wall of the protruding pieces 121*e* may be a tapered form so that the protruding pieces 121*e* can easily be inserted into the outlet opening 111*f*.

The lock ring 130 is rotatably mounted over the male luer part 111 of the outer cylinder 110 and the outer periphery of the ring holding part 112. The lock ring 130 is provided with the first internal threaded part 131 on the inner periphery from the left side end in the figure as well as an engagement part 132 protruding in the radial direction in the right end side in the figure. The inner peripheral surface of the engagement part 132 is placed to face to the outer peripheral surface of the second cylinder 112*b* of the ring holding part 112. The inner diameter of the engagement part 132 is smaller than the outer diameter of the first cylinder 112*a* and the outer diameter of the third cylinder 112c and greater than the outer diameter of the second cylinder 112b. Therefore, the engagement part 132 is movable between the first step 112d and the second step 112e in the axial direction of the outer cylinder 110, while the further movement thereof over that range is controlled by both steps 112d and 112e.

As shown in FIGS. 3 and 4, the female luer connector 10 is in a bell like shape where the inner diameter is increased from the left to the right in the figures. Within the female luer connector 10, a flow path space 15 is formed and opened at the larger diameter end side thereof. The tapered inner peripheral wall 10a of the female luer connector 10 forming the flow path space 15 is formed to be tapered such that the inner diameter is increased from the left to the right in the figures. The tapered inner peripheral wall 10a may be of a portion having a taper angle and a diameter corresponding to the tapered outer peripheral wall 111b of the male luer part 111. Also, near the larger diameter end of the outer periphery of the female luer connector 10, protrusions 10b outwardly protruded in the radial direction. The protrusions 10b are symmetrically provided at two positions on the outer periphery of the female luer connector 10, thereby helically engaging with the first inner threaded part 131 of the lock ring 130 when the female luer connector 10 is coupled to the male luer connector 101.

In the above configuration, when the male luer connector 101 is not coupled to the female luer connector 10, the condition as shown in FIGS. 3 and 4 is maintained. In this condition, the outlet opening of the male luer part 111 is liquid tightly sealed by the protruding pieces 121e formed by the body tube 121 as well as the first opening 121b of the body tube 121 is liquid tightly sealed by the column 111g of the male luer part 111. Accordingly, even though the liquid within the flow path space in the first tube member T1 connected to the body tube 121 at the second opening 121c is entered into the flow path 121a in the body tube 121 through the second opening 121c, the liquid can not be leaked to the exterior because the first opening 121b and the outlet opening 111f are liquid tightly sealed. As well as, the liquid is not mixed into the male luer connector 101 from the outside thereof.

Further, when priming is performed in such sealing condition, to the column 111g, a gas permeable filter through which the gas can be passed and the liquid can not be passed may be attached. Therefore, the gas such as air resided within the flow path 121a, the flow path of the first tube member T1 connected to the body tube 121 can be discharged to the exterior through the filter even with that sealing condition, thereby performing the priming operation. In this time, the liquid is not leaked at the priming because the liquid can not be passed through the filter.

When the male luer connector 101 is coupled to the female luer connector 10, the female luer connector 10 is moved in the axial direction to the right in the figures so as to close to the male luer connector 101 while the axis of the female luer connector 10 is aligned with that of the male luer connector 101 from the condition as illustrated in FIGS. 3 and 4. At this time, by the movement of the female luer connector 10 in the axial direction to the right in the figures, the male luer part 111 is entered the flow path space 15 within the female luer connector 10 and the larger diameter end surface of the female luer connector 10 is contacted with the tip end surface of the arms 122b outwardly projected to the outside of the male luer part along the axial direction thereof. In this contact condition, when the female luer connector 10 is further moved to the right in the figures, the arms 122b contacted with the end surface of the female luer connector 10 is coopera-tively moved to the right in the figures and the body tube 121 for fixing the support arm 122 having the arms 122b is also moved in the axial direction to the right in the figures.

By such a movement of the body tube 121, the protruding pieces 121e are deviated from the outlet opening 111f to provide a condition where the outlet opening 111f is released from the liquid tightly seal by the protruding pieces 121e. As well as, the column 111g is deviated from the first opening 121b to provide a condition where the first opening 121b is released form the liquid tightly seal by the column 11. When the female luer connector 10 is moved further to the right in the figures, the tapered outer peripheral wall 111b of the male luer part 111 is liquid tightly contacted with the tapered inner peripheral wall 10a of the female luer connector 10 to couple the male luer connector 101 to the female luer connector 10. In this condition, the first inner threaded part 131 of the lock ring 130 is aligned with the protrusions 10b of the female luer connector 10 in the axial direction and the lock ring 130 is rotated. Then, the female luer connector 10 is helically engaged with the lock ring 130 to provide firm connection between the female luer connector 10 and the male luer connector 101.

Figure 13:
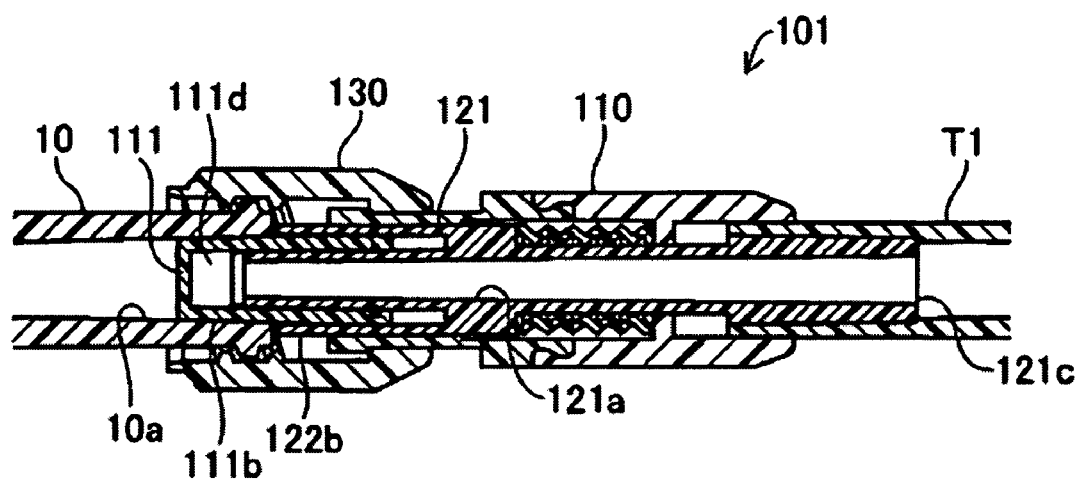
FIG. 13 is a cross sectional view in A-A of FIG. 2 where the male luer connector of the first embodiment is coupled to the female luer connector in accordance with the invention.
Figure 14:
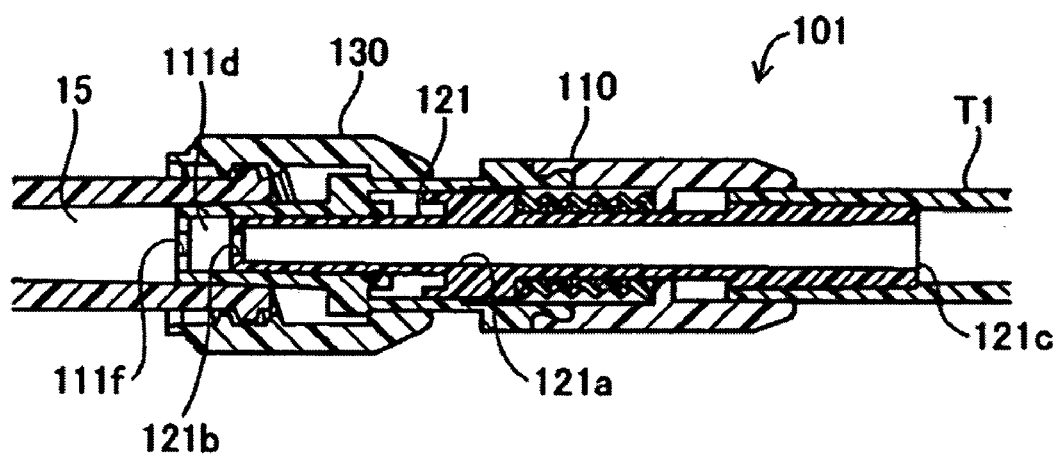
FIG. 14 is a cross sectional view in B-B of FIG. 2 where the male luer connector of the first embodiment is coupled to the female luer connector in accordance with the invention.

The cross sectional views illustrating the completed coupling between the male luer connector 101 and the female luer connector are shown in FIGS. 13 and 14 (FIG. 13 is a cross sectional view in A-A of FIG. 2 and FIG. 14 is a cross sectional view in B-B of FIG. 2, respectively). As shown in FIGS. 13 and 14, the tapered inner peripheral wall 10a of the female luer connector and the tapered outer peripheral wall 111b of the male luer part 111 are liquid tightly contacted with each other to prevent the liquid from leaking between both walls to the exterior. Also, the arms 122b is pressed to the larger diameter end of the female luer connector 10 to backwardly move the body tube 121 within the outer cylinder 110 to the right direction in the figures, whereby the outlet opening 111f of the male luer part 111 and the first opening 121b of the body tube 121 are placed so as to be remote from each other (see FIG. 14).

In this condition, the liquid within the flow path of the first tube member T1 connected to the second opening 121c of the body tube 121 is admitted into the flow path 121a in the body tube 121 from the second opening 121c and conducted to the inner space 111d in the male luer part 111 through the first opening 121b. Further, the liquid enters the flow path space 15 in the female luer connector 10 from the inner space 111d through the outlet opening 111f and, then, flows within the second tube member (not shown) connected to the female luer connector 10. In this way, the flow communication between two tube members can be achieved by the connection of the male luer connector 101 to the female luer connector 10.

Figure 15:
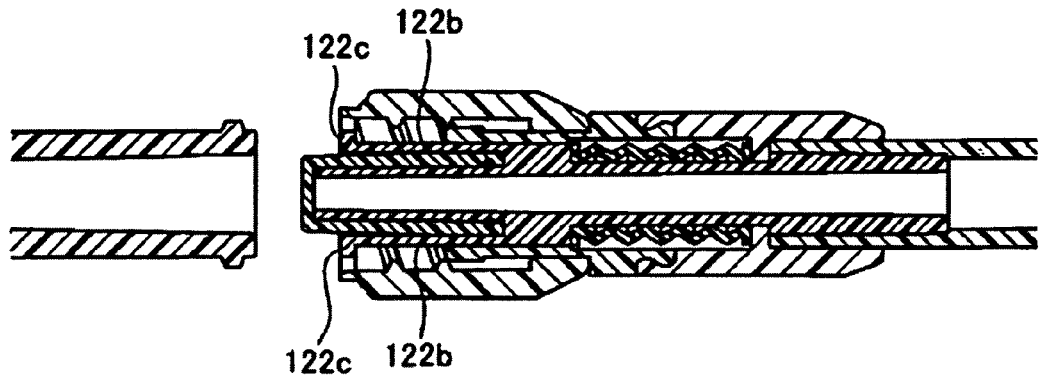
FIG. 15 is a cross sectional view in A-A of FIG. 2 illustrating the modified first embodiment of the male luer connector.
Figure 16:
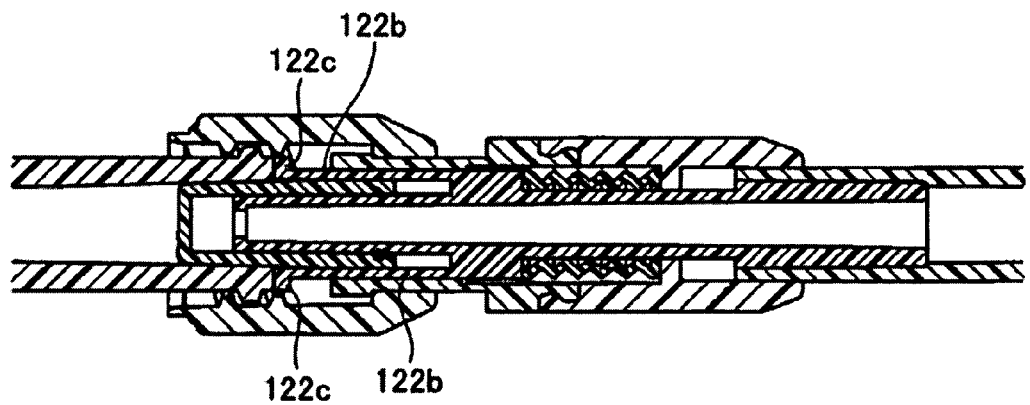
FIG. 16 is a cross sectional view in A-A of FIG. 2 where the male luer connector of the modified first embodiment is coupled to the female luer connector in accordance with the invention.

FIG. 15 is a cross sectional view illustrating a modified embodiment of the embodiment explained in above in which the arms have been modified. This cross sectional view is a cross section at A-A in FIG. 2. As shown in FIG. 15, at the tip portion of the arms 122b in this embodiment, a contact part 122c is formed to extend further in the radial direction of the male luer part. Therefore, as shown in FIG. 16, it can be sure that the contact part 122c is contacted with the end surface of the female luer connector 10 to cooperatively move the body tube 121 with the motion of the female luer connector 10.

As described in above, the male luer connector 101 of the embodiment in accordance with the present invention is configured such that one end of the body tube 121 is inserted into the inner space 111d in the male luer part 111 and two protruding pieces 121e provided to this one end are axially moved to liquid tightly seal the outlet opening 111f of the male luer part 111, therefore, the outlet opening 111f can be maintained bacteria free while the male luer connector 101, 102 is unused. Further, the liquid tightly sealing and opening the outlet opening 111f can be made by moving two protruding pieces 121e within the inner space 111d of the male luer part 111, and two pieces 121e can not be exposed to the outer of the male luer part 111, in particular, to the area beyond the smaller diameter surface 111e of the male luer part 111. Accordingly, the outlet opening 111f can smoothly be liquid tightly sealed or opened without interference with the other components by these protruding pieces 121e.

When the outlet opening 111f is liquid tightly sealed by these protruding pieces 121e, the first opening 121b of the body tube 121 is also liquid tightly salad by the column 111g of the male luer part 111. In this way, by liquid tightly sealing the openings of the male luer part 111 and the body tube 121 by each other, the leakage of the liquid within the body tube 121 as well as the contamination by another liquid medicine from the outside into the inner space 111d of the male luer part 111 can certainly be prevented.

Moreover, the body tube 121 is cooperatively moved with the motion of the female luer connector 10 by the support arm 122 fixed to the body tube 121 to open the outlet opening 111f. Therefore, this cooperation of the moving operation of the female luer connector 10 with the opening operation the outlet opening 111f makes the coupling operation of the male luer connector 101 and the female luer connector 10.

Second Embodiment

Next, the second embodiment of the invention will be explained. In this embodiment, a filter is provided at the tip end surface of the body tube 121 to allow priming while the outlet opening 111f of the male luer part 111 is liquid tightly sealed by the body tube 121, as well as, the lock ring 130 is helically engaged with the body tube 121 to allow the body tube 121 being moved relative to the male luer part 111 by the rotation of the lock ring 130, which are characteristics in this embodiment. The embodiment will be explained with these characteristics as a main part in below.

Figure 17:
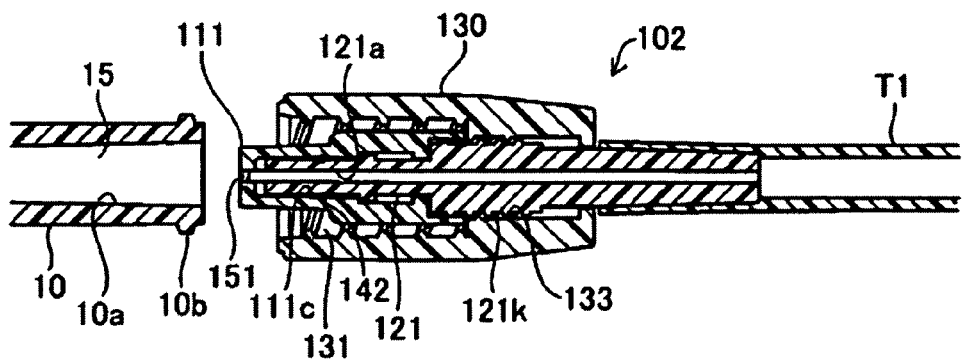
FIG. 17 is a cross sectional view illustrating the male luer connector of a second embodiment in accordance with the invention.

FIG. 17 is a cross sectional view illustrating the male luer connector 102 of the embodiment in accordance with the invention. This cross sectional view is a cross section at A-A in FIG. 2. As shown in this figure, at the tip end surface of the body tube 121 (the left end in the figure), a filter 151 is provided. The filter 151 is a gas permeable filter including a number of fine pores formed therein thorough which gases can be passed but liquids can not be passed. A porous sintered body and the like may be employed as such a filter having these properties in above.

Figure 18:
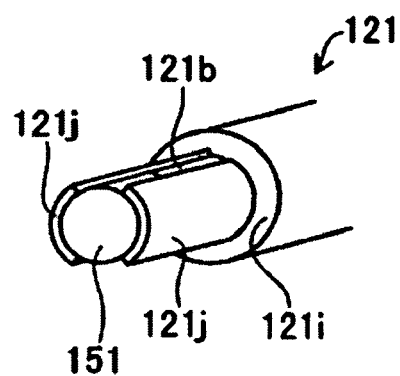
FIG. 18 is a perspective view illustrating the tip end of the body tube of the second embodiment in accordance with the invention.
Figure 19:
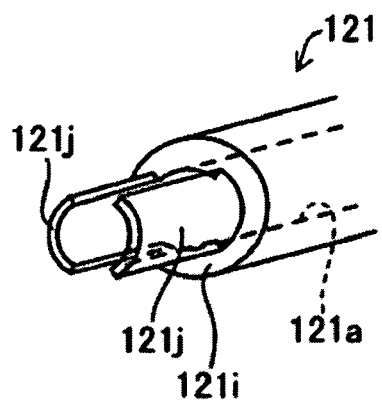
FIG. 19 is a perspective view illustrating the body tube without the filter of the second embodiment in accordance with the invention.

FIG. 18 is an enlarged perspective view illustrating near the tip end of the body tube 121; FIG. 9 is an enlarged perspective view illustrating near the tip end of the body tube 121 of FIG. 18 from which the filter 151 is eliminated. As shown in FIG. 19, at the tip end of the body tube 121, two protruding parts 121j is formed along the axis from an end surface 121i to which the flow path 121a in the body tube 121 is opened. These tow protruding parts 121j are symmetrically provided relative to the axis of the body tube 121 and configured so as to be a curved wall arc to surround the opening of the flow path 121a, while two protruding parts 121j are formed as spaced apart from each other by the predetermined distance not to cover the whole periphery of the opening thereby.

Further, as shown in FIG. 18, a cylindrical filter 151 is placed within a space surrounded by inner walls of two protruding parts 121j so as not to be rid out therefrom. Also, the filter 151 is attached to the tip end of the protruding parts 121j as spaced apart from the end surface 121i by the predetermined distance. Therefore, in the area surrounded by the filter 151 and tow protruding parts 121j, a gap is formed to be the first opening 121b of the body tube 121.

And, as shown in FIG. 17, to the body tube 121, an outer threaded part 121k is formed at generally near the center thereof. Corresponding to this outer threaded part 121k, a second inner threaded part 133 is formed to the inner periphery of the lock ring 130. The second threaded part 133 is formed so as to have the same lead as that of the first inner threaded part 131. That is, when the first inner thread portion 131 is a right hand screw, then, the second inner threaded part 133 is also a right hand screw, conversely, when the first inner thread portion 131 is a left hand screw, then, the second inner threaded part 133 is also a left hand screw. The second threaded part 133 is helically engaged with the outer threaded part 121k of the body tube 121 while the lock ring 130 is installed to the body tube 121. The other components are not explained because they are the same as those of the first embodiment in above.

In the male luer connector 102 having such a configuration, when the lock ring 130 is rotated in the predetermined in the direction about the axis (for example, clockwise direction), the outer threaded part 121k of the body tube 121 is helically engaged with the second inner threaded part 133 to move the body tube 121 to the left in the figure. Then, the tip end of the body tube 121 enters the outlet opening 111f of the male luer part 111. At that time, the configuration of the outlet opening 111f of the male luer part 111 is almost the same as that of the cross section of the filter 151 as combined with two protruding parts 121j. Accordingly, the outlet opening 111f can be liquid tightly sealed by the protruding parts 121j and the filter 151.

When the priming is performed in the condition in above, the air resided within the flow path 121a of the body tube 121 is discharged to the exterior through the filter 151. On the other hand, since the liquid within the flow path 121a can not be passed through the filter 151, the liquid is not discharged to the exterior during the priming. Also, since the O ring 142 is attached between the inner wall 111c of the male luer part 111 and the outer periphery of the body tube 121, there is not leakage of the liquid from the gap between the inner wall 111c and the outer periphery of the body tube 121.

Figure 20:
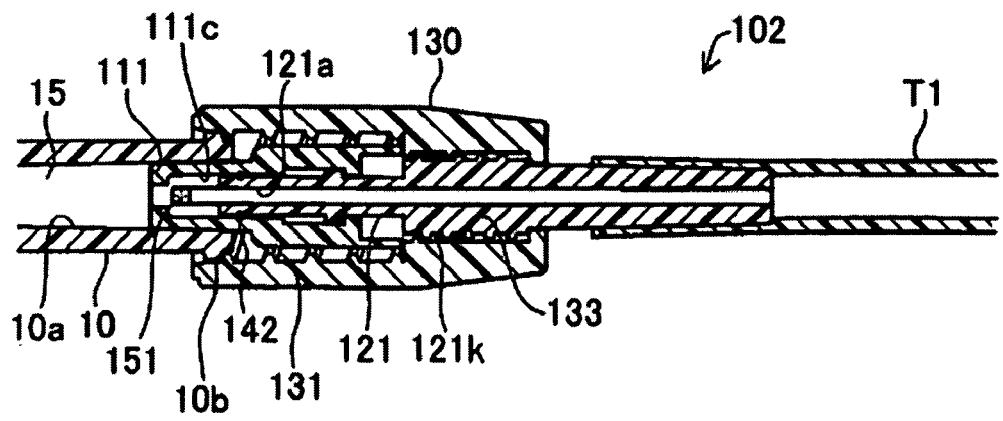
FIG. 20 is a cross sectional view illustrating the male luer connector of the second embodiment in accordance with the invention connected to the female luer connector.

After the completion of the priming, the male luer connector 102 is coupled to the female luer connector 10, and, then, the lock ring 130 is rotated in the opposite direction (for example, counterclockwise) to the predetermined direction about the axis while the protruding part 10b formed to the female luer connector 10 is contacted with the first inner threaded part 131 of the lock ring 130. Thus, the protruding part 10b formed to the female luer connector 10 is helically engaged with the first inner threaded part 131 by the rotation of the lock ring 130 by moving in the direction where the female luer connector 10 is closed to the male luer connector 102, whereby the female luer connector 10 is contacted with the male luer connector 102. Further, since the second inner threaded part 133 of the lock ring 130 is helically engaged with the outer threaded part 121k of the body tube 121, the body tube 121 is also moved about the axis by the rotation of the lock ring 130. In this time, since the lead of the second inner threaded part 133 is formed so as to be the same as that of the first inner threaded part 131, the body tube 121 accompanied by the rotation of the lock ring 130 is moved in the direction where the female luer connector 10 is advanced to deviate from the lock ring 130. By this motion, as shown in FIG. 20, the protruding part 121 of the body tube 121 and the filter 151 is separated from the outlet opening 111f of the male luer part 111 to open the outlet opening 111f. Therefore, the liquid from the low path 121a of the body tube 121 is conducted to the female luer connector 10 through the outlet opening 111f in this condition. Thus, the communication of the liquid has been achieved.

As described in above, in the male luer connector 102 of the embodiment in accordance with the invention, the filter 151 through which the gas can be passed and the liquid can not be passed is provided at the tip end of the body tube 121 and two protruding parts 121j for sandwiching the filter 151, whereby the outlet opening 111f of the male luer part 111 can be liquid tightly sealed. Accordingly, the priming can be performed while the outflow of the liquid can be prevented by the filter 151. Therefore, the gas such as air residing within the male luer part 111, the body tube 121 or the tube members connected to the body tube 121 can bed discharged to the exterior while preventing the liquid leakage.

Further, the lock ring 130 is provided with the first inner threaded part 131 to be engaged with the female luer connector 10 and the second inner threaded part 133 to be engaged with the body tube 121, whereby the male luer connector 102 is fixed to the female luer connector 10 and the outlet opening 111f is opened by moving the body tube 121 at the same time with the rotation of the lock ring 130.

Third Embodiment

FIGS. 21 to 24 show the male luer connector 201 of the third embodiment in accordance with the invention. The male luer connector 201 comprises a connector body 210 attached to the tip end of a first tube member T2; a male luer part 220 provided at the tip end of the connector body 210; a moving body tube 230 movably provided within the male luer part 220; a lock ring 240 attached to the outer periphery of the tip end of the connector body 210; and an elastic seal member 250 provided within the center of the connector body 210.

The connector body 210 comprises a generally cylindrical basal connector 211 in which the diameter is gradually increased from the basal end to be connected to the first tube member T2 to the tip end; a stepped cylindrical tip end support 212 forwardly extended from the tip end of the basal connector 211. The basal connector 211 is formed to have a flow path 211a therein for flowing a liquid medicine and the tip end side of the basal connector 211 is formed into a space 211b having a large diameter. Further, at the outer peripheral of the flow path 211a in the rear side of the basal connector 211, a ring shaped recessed fixer 213 extended from the rear side to the tip end side is formed, in which the tip end of the first tube member T2 is engaged with the recessed fixer 213 to connect the basal connector 211 to the first tube member T2. Further, at the tip end outer periphery of the basal connector 211, a step 214 for the imposition having the smaller outer diameter is formed.

The tip end support 212 comprises a fixing part 215 having a larger diameter fixed to the step 214 of the basal connector 211 and a support 216 having a smaller diameter extended from the center of the tip end of the fixing part 215. The fixing part 215 is provided with a smaller diameter part 215b that is formed within a lager diameter part 215a with the step 214 inserted therein, in which both the diameter and the axial length are smaller than those of a larger diameter part 215a. These larger diameter part 215a and smaller diameter part 215b are connected to each other at the fore end and between the larger diameter part 215a and the smaller diameter part 215b at the rear end are opened. Then, the elastic seal member 250 is attached between the larger and smaller diameter parts 215a and 215b with its periphery is inserted between them.

In other word, the periphery of the elastic seal member 250 is inserted between the larger and the smaller diameter parts 214a and 215b to attach the elastic seal member 250 to the fixing part 215, and the step 214 of the basal connector 211 is inserted into the larger diameter part 215a of the fixing part 215 in the condition to secure the fixing part 215 to the basal connector 211, thereby fixing the elastic seal member 250 between the fixing part 215 and the basal connector 211. In this case, the portion positioned at the opening side between the larger diameter part 215a and the smaller diameter part 215b in the elastic seal member 250 is prevented from releasing from the position between the larger diameter part 215a and the smaller diameter part 215b by pressing by the tip end of the step 214.

The elastic seal member 250 is comprised of a plate like rubber having elastic and stretch properties. At the center of the member 250, a stretch hole 251 to open or close by stretching thereof is formed. Accordingly, the elastic seal member 250 is stretched as applied the predetermined pressure in the backward at the front surface thereof to open the stretch hole 251, and, conversely, is shrunk by releasing the pressure to close the stretch hole 251. When the stretch hole 251 is closed, the flow path 211a in the basal connector 211 is blocked not to flow the liquid medicine. Further, at the central part on the rear surface of the elastic seal member 250 (around the stretch hole 251), a corn shaped small projection 252 backwardly projecting is formed. By the projection 252, the pressure applied to the central part of the elastic seal member 250 can be dispersed when the liquid medicine is filled in the flow path 211a, thereby improving the pressure residence of the elastic seal member 250.

The support 216 is formed into a cylinder in which the inner diameter is the same as that of the smaller diameter part 215b of the fixing part 215, the outer diameter slightly smaller than that of the smaller diameter part 215b and the axial length longer than that of the smaller diameter part 215b. At the portion other than the tip end on the outer peripheral surface of the support 216, a recess 216a for slide having a slightly smaller outer diameter than the tip end portion. Also, within the support 216, a generally cylindrical male luer part 220 is provided with a space from the inner peripheral surface of the support 216 and a projected tip end from the tip end opening of the support 216. The male luer part 220 is connected to the support 216 through a ring shaped wall 216b (see FIG. 22) and formed such that the tip end portion of the male luer part 220 can be liquid tightly contacted with the tapered inner peripheral wall 20a of the female luer connector 20.

Figure 22:
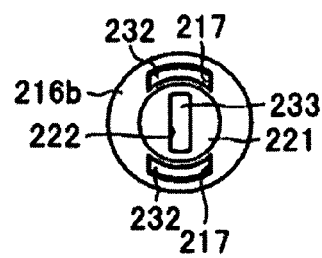
FIG. 22 is a front view of the support of the connector body and the male luer part.

The male luer part 220 is formed into a tapered cylinder tapered as to the tip end side (the left side in the figure) and provided with a smaller diameter end surface 221 having the smallest outer diameter. Further, the basal end of the male luer part 220 (the right side in the figure) is opened from which the moving body tube 230 as described in below is inserted into the male luer part 220. FIG. 22 shows the support 216 and the male luer part 220 from the front side, in which a narrow outlet opening 222 is formed at the smaller diameter end surface 221 of the male luer part 220. Also, at the wall 216b, a pair of arc shaped windows 217 having a convex at the outer thereof to sandwich the outlet opening 222 longitudinally.

The moving body tube 230 comprises a generally cylindrical body within which a flow path 231 is formed and a pair of support arms 231 is formed on the outer periphery thereof. The flow path 231 corresponds to the communication flow path of the invention and is formed along with the axis of the moving body tube 230 which both ends are opened. Also, from the center of the tip end surface of the moving body tube 230, a protruding piece for liquid tightly sealing the outlet opening 222 by entering into the outlet opening 222 of the male luer part 220 is forwardly projected, and at both end portion of the protruding piece 233 on the tip end surface of the moving body tube 230, an opening is formed (not shown). This opening is occluded by the smaller diameter end surface 221 as the moving body tube 230 is forwardly moved.

The pair of support arms 232 is extended from the rear end to the outer peripheral surface of the moving body tube 230 with the predetermined space maintained. The pair of support arms 232 is symmetrically mounted to the moving body tube 230 with a space of the angle of 180 degrees and the tip ends thereof are extended not to over the opening at the tip end of the moving body tube 230. The moving body tube 230 configured in this way is axially movably inserted into the male luer part 220, and tip ends of the support arms 232 are projected to the outside through the pair of the windows 217 formed to the wall 216b. And, between near the center of the inner wall of the male luer part 220 and the outer peripheral surface of the moving body tube 230, the O ring 235 is fitted.

The moving body tube 230 is configured such that when the moving body tube 230 is forwardly moved as activated by the elasticity of the elastic seal member 250 and the protruding piece 233 is entered into the outlet opening 222 to liquid tightly seal the outlet opening 222, the stretch hole 251 of the elastic seal member is also shrunk to close. The male luer connector 201 and the other components of the female luer connector 20 connected to the male luer connector 201 are the same as those of the first embodiment described in above, therefore, the explanation thereof is omitted while the same components are referred to the same indications.

Figure 21:
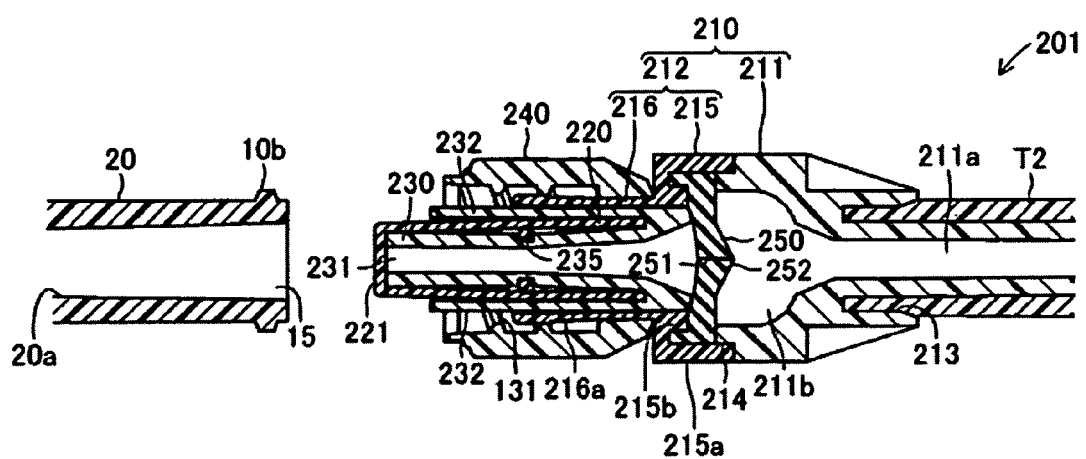
FIG. 21 is a cross sectional view illustrating the male luer connector of a third embodiment in accordance with the invention connected to the female luer connector.
Figure 23:
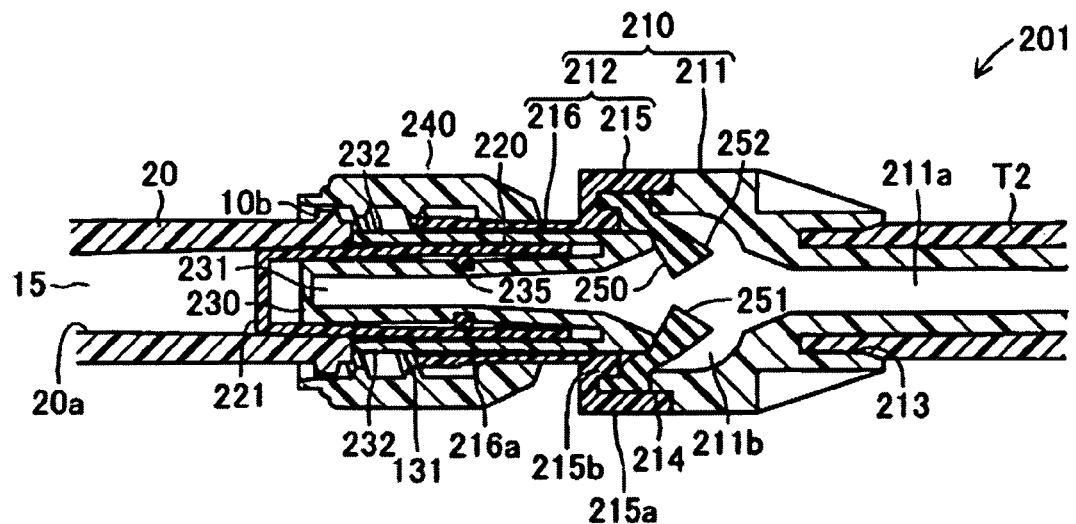
FIG. 23 is a cross sectional view illustrating the male luer connector of the third embodiment in accordance with the invention connected to the female luer connector.

When the male luer connector 201 configured in this way is connected to the female luer connector 20, first, as shown in FIG. 21, the tip end of the male luer connector 201 is approached to the tip end opening of the female luer connector 20 to opposed to each other. Then, the male luer part 220 is entered into the female luer connector 20 such that, as shown in FIG. 23, the tapered inner peripheral wall 20a of the female luer connector 20 is liquid tightly contacted with the outer peripheral surface of the tie end side of the male luer part 220. At that time, the tip end of the support arms 232 are contacted to the tip end surface of the female luer connector 20 to backwardly moved the moving body tube 230 within the male luer part 220. Accordingly, the outlet opening 222 and the stretch hole 251 of the elastic seal member 250 are opened.

Figure 24:
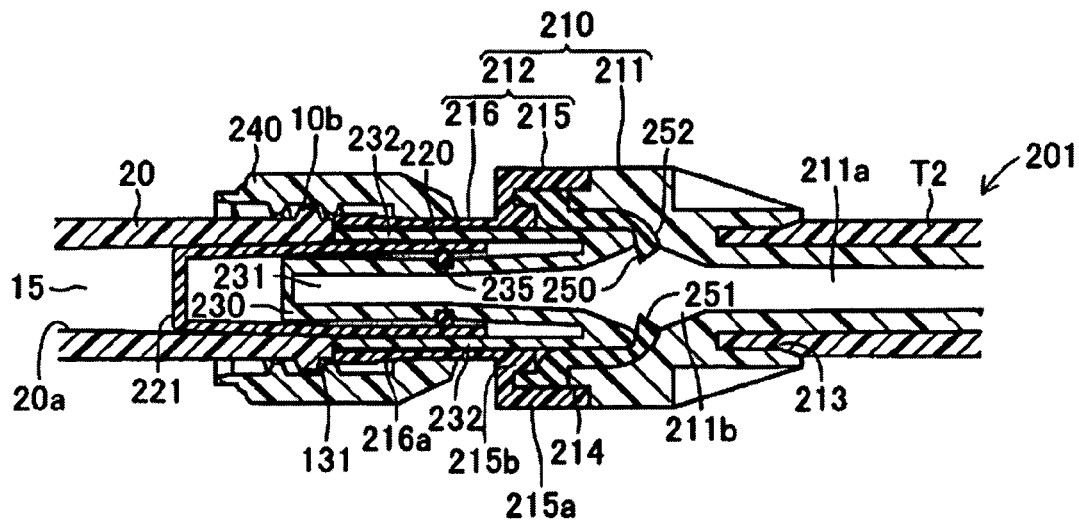
FIG. 24 is a cross sectional view illustrating the male luer connector of the third embodiment in accordance with the invention connected to the female luer connector.

Then, after the first inner threaded part 131 of the lock ring 240 is contacted to the projection 10b of the female luer connector 20, they are helically engaged with each other by rotating the lock ring 240 about the axis in the predetermined direction. And, when the engagement of the first inner threaded part 131 and the projection 10b are proper, as shown in FIG. 24, the female luer connector 20 and the male luer connector 201 are communicated with each other such that no leakage of the liquid is occurred.

As described in above, in the male luer connector 201 of the embodiment in accordance with the invention, when the male luer connector 201 is not connected to the female luer connector 20, the male luer part 220 is forwardly activated to close the outlet opening 222 by the elasticity as well as the stretch hole 251 of the elastic seal member 29 is also closed. Accordingly, the liquid medicine within the flow path 211a of the male luer connector 201 is prevented from entering into the flow path 213 of the moving body tube 230, as well as, from being spilled out from the outlet opening 222 of the male luer part 220 to the exterior. As a result, it can be prevented that the liquid medicine is spilled out to adhere the outer surface of the male luer connector 201, or bacteria is brood at the adhered portion. Further, the spilled the liquid medicine can be reduced to save the liquid medicine.

Moreover, when the tapered inner peripheral wall 20a of the female luer connector 20 and the outer peripheral surface of the male luer part 220 are liquid tightly contacted with each other by admitting the male luer part 220 to the female luer connector 20, the elastic seal member 250 is pushed by the mobbing body tube 230 to open the stretch hole 251. Accordingly, the liquid medicine can be flowed from the first tube member T2 to the second tube member connected to the female luer connector 20 by the proper flow rate without leakage thereof to the exterior. Also, when the male luer connector 201 is released form the female luer connector 20, the flow path 211a in the male luer connector 201 is occluded because the stretch hole 251 is closed by the restoring force of the elastic seal member 250. In this time, the moving body tube 230 is forwardly moved to occlude the outlet opening. Accordingly, when the male luer connector 201 is released form the female luer connector 20, there is no fear to spill out the liquid medicine from the outlet opening 222 of the male luer part 220. The other effects of the male luer connector 201 are the same as those of the male luer connector 101 described in above. In the male luer connector 201 of this embodiment, the gas permeable filter included in the modified embodiment in above or other mechanisms and members may be employed.

In summary, the present invention provides a closable male luer connector in which an inner portion within the spigot of the connector is movable from a sealing position to an open position on connection of the connector to a female luer connector. The movement of the inner portion may be caused by, for example, action of the female connector on a projecting arm or a screw thread arrangement.

We claim:

1. A sealable male luer connector, comprising:
   a tapering first tubular part for forming a seal with a corresponding part of a female luer connector, the first tubular part having an end region including a cross bar and through holes on either side of said cross bar;
   a second tubular part disposed at least partially within said first tubular part, wherein said second tubular part is movable relative to said first tubular part from a first sealing position to a second non-sealing position, the second tubular part having an end region including a central groove and sealing faces on either side of said groove such that when said second tubular region is in said first sealing position, said cross bar is positioned within said groove and said sealing faces seal said through holes; and
   actuating means for urging said second tubular part into said non-sealing position when said male luer connector is connected to said female luer connector.

2. The male luer connector according to claim 1, wherein said actuating means includes at least one arm extending substantially parallel to a longitudinal axis of said second tubular part and affixed to said second tubular part, and wherein when said second tubular part is inserted at least partially into said first tubular part, said at least one arm extends externally of said first tubular part.

3. The male luer connector according to claim 2, wherein said actuating means includes two arms and wherein when said male luer connector is attached to said female luer connector, said arms are pushed in a longitudinally axial direction by said female luer connector.

4. The male luer connector according to claim 3, further including biasing means for urging said second tubular part toward said first sealing position.

5. A sealable male luer connector, comprising:

a tapering first tubular part for forming a seal with a corresponding part of a female luer connector;

a second tubular part disposed at least partially within said first tubular part, wherein said second tubular part is movable relative to said first tubular part from a first sealing position to a second non-sealing position;

actuating means for urging said second tubular part into said non-sealing position when said male luer connector is connected to said female luer connector, said actuating means including an outer rotatable lock ring having an internal screw thread in combination with a corresponding screw thread on an outer surface of said second tubular part such that rotation of said lock ring in a first direction causes said second tubular part to move from said first sealing position to said open position and rotation thereof in a second direction, opposite to said first direction, causes said second tubular part to move from said open position to said sealing position.

6. The male luer connector according to claim 5, wherein said second tubular part comprises a filter, said filter being air permeable and water non-permeable.

7. A male luer connector attached to a first tube and connectable to a female luer connector for providing a flow channel between said first tube and a second tube attached to said female luer connector, said male luer connector comprising:

a tube member having openings for providing said flow channel; and a male luer part including:
a tapered outer peripheral wall tapering toward a tip end for providing a seal with a tapered inner peripheral wall of said female luer connector,
a side wall having an inner wall forming an inner space, an outlet opening formed at a smaller diameter surface of the side wall,
a column connected to the smaller diameter surface, said column dividing the outlet opening, and
a tube member sealing arrangement formed at the outlet opening or the inner wall for providing a liquid tight seal with the tube member as the tube member is moved toward the outlet opening.

* * * * *